(12) United States Patent
Balczewski et al.

(10) Patent No.: US 6,880,085 B1
(45) Date of Patent: Apr. 12, 2005

(54) SECURITY SYSTEM FOR IMPLANTABLE MEDICAL DEVICES

(75) Inventors: Ronald A. Balczewski, Roseville, MN (US); Karen Lent, Stillwater, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 946 days.

(21) Appl. No.: 09/703,746

(22) Filed: Nov. 1, 2000

(51) Int. Cl.[7] .................................................. H04L 9/00
(52) U.S. Cl. ...................... 713/182; 713/183; 713/193; 713/200; 713/201
(58) Field of Search .......................... 713/182, 183, 713/193, 200, 201

(56) References Cited

U.S. PATENT DOCUMENTS

| | | | |
|---|---|---|---|
| 5,607,458 A | | 3/1997 | Causey, III et al. |
| 5,792,201 A | | 8/1998 | Causey, III et al. |
| 6,004,276 A | | 12/1999 | Wright et al. |
| 6,092,193 A | * | 7/2000 | Loomis et al. .............. 713/193 |
| 6,108,583 A | | 8/2000 | Schneck et al. |
| 6,119,229 A | * | 9/2000 | Martinez et al. ............ 713/200 |
| 6,128,148 A | * | 10/2000 | Platte et al. .................. 360/60 |

\* cited by examiner

*Primary Examiner*—Thomas R. Peeso
(74) *Attorney, Agent, or Firm*—Thomas J. Nikolai; Nikolai & Mersereau, P.A.

(57) ABSTRACT

A security system for programmable medical devices is provided. Such devices have a variety of features at least some of which are only enabled if a proper password is provided. Different levels of security are provided to protect the patent from inadvertent or unintended reprogramming or from deliberate, but unauthorized efforts to reprogram the device.

46 Claims, 4 Drawing Sheets

SECURITY SYSTEM FOR IMPLANTABLE MEDICAL DEVICES

BACKGROUND OF THE INVENTION

I. Field of the Invention

This invention relates to implantable, programmable medical devices, for example heart pacemakers and defibrillators. More particularly, it relates to a rights-based security system for regulating the programming of such devices.

II. Description of the Prior Art

Implantable pacemakers have been in use for decades to regulate the beating of the human heart. The earliest pacemakers were nothing more than a pulse generator and a battery designed to deliver electrical pulses to the heart at a fixed rate. Soon thereafter, pacemakers were made available that had two modes of operation. The pacemaker could be switched from one mode to the other by holding a magnet over the pacemaker to actuate a switch.

In the 1960's, throughout the 1970's and into the 1980's, pacemaker manufacturers introduced a variety of pacemaker products that could be programmed through the use of radio frequency or magnetic pulses. Such pacemakers had an operate mode and a programming mode. To prevent inadvertent reprogramming of the pacemaker as a result of ambient electrical or magnetic noise, the circuits for these pacemakers included a "combination lock". Such pacemakers would only go into the programming mode if the "combination lock" was opened. The "combination lock" typically would only be opened if the correct number of pulses were received within a plurality of discrete time periods.

Until very recently, a patient being treated with a pacemaker would periodically travel to a clinic for assessment and, if necessary, reprogramming. Given the face-to-face interaction between the patient and the medical provider, and the short range transmission of data, security was not a significant issue. With modern data transmission technology, such assessment or program modification can be done from very remote locations. Such assessment and programming could even be done via the Internet.

Given this global data transmission range, the interconnection of devices to the Internet, and the fact that not all people are pure of heart, there is a real need for added security. Life-threatening situations could arise if hackers or anyone with a programmer were allowed to reprogram heart pacemakers or if Internet users were able to infect the programming of a pacemaker with viruses. Similar problems could occur if unauthorized people were permitted to download in an unauthorized fashion history or treatment data from such devices. Without sufficient security, someone knowing the telemetry protocol for retrieval of data from or programming for the implantable device could harm the patient, blackmail the patient, or blackmail the company which supplies the implantable device. There is, therefore, a need to provide a security system which will safeguard pacemakers and other programmable medical devices not only from inadvertent reprogramming, but also from the deliberate efforts of those with evil intent. At the same time, the data must be readily accessible and the device readily reprogrammable in emergency situations, to safeguard the patient's life and health. The present invention provides such a system.

SUMMARY OF THE INVENTION

In accordance with the present invention, a programmable, implantable medical device such as a cardiac rhythm management device, is provided which is equipped with a security system which prevents reprogramming of the device by anyone but authorized medical personnel. The system incorporates multiple levels of security based upon passwords or key codes and can be turned on or off based upon physician or user preferences. The device can also be operated in various modes or permit various features to be accessed without the password if desired. Accessing certain other modes or features does require the password. To further enhance security, the system can refuse to accept additional password entry efforts for a period of time after a predetermined number of efforts have failed. The system can also maintain a log of each programmer that has gained access (or attempted to gain access) to the system. The system can also emit an alarm tone after multiple incorrect passwords have been tried. Finally, to permit access if a password has been lost or corrupted, a master password or preferably a complex, time-consuming "back door" procedure, can be used.

Such a system offers a variety of advantages. It provides a security-based access to various feature sets of the medical device. It provides multiple levels of security.

It provides the ability to alter the feature sets available at various levels of security. It should also provide the opportunity to provide additional passwords and securely store these additional passwords for use at a later time. Such a system allows the medical device to be reprogrammed from remote locations by authorized medical personnel. At the same time, it protects the patient from inadvertent or unauthorized reprogramming of the device.

BRIEF DESCRIPTION OF THE DRAWINGS

The various advantages of the present invention will become more clear from a reading of the following detailed description of the preferred embodiment in view of the drawings in which.

DETAILED DESCRIPTION OF THE PREFERRED EMBODIMENTS

Various types of implantable medical devices have been developed over the past 40 years. Significant advances have been made in the field of cardiac rhythm management. Therefore, the following description of the present invention is provided in terms of cardiac rhythm management devices. Those skilled in the art will recognize that this invention can be applied to other medical devices as well.

Figure 1:
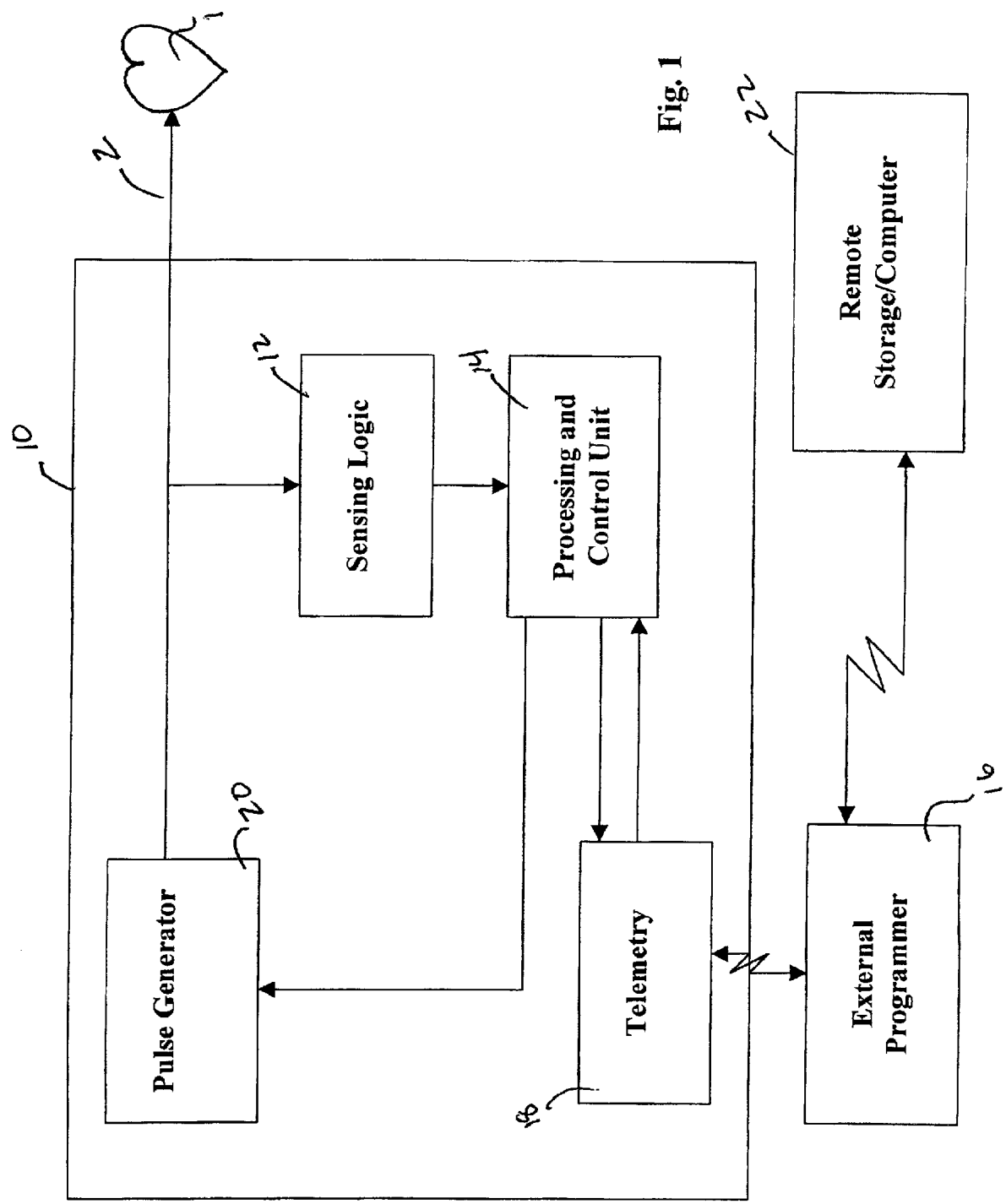
FIG. 1 is a schematic diagram showing a cardiac rhythm management device, programmer and remote computer.

FIG. 1 shows a cardiac rhythm management device 10 attached to the heart 1 by a lead 2. The rhythm management device 10 itself, typically will include sensing logic 12 which senses the electrical activity of the heart 1 and sends corresponding signals to a processing and control unit 14. Processing and control units 14 in use today typically include processing means and are programmable. To program the processing and control unit 14, typically two other devices are required—an external programmer 16 and internal telemetry 18 which is used to transmit programming signals and other data between the processing and control unit 14 and the external programmer 16. The processing and control unit 14 uses the instructions and parameters with which it has been programmed, along with the data received from the sensing logic 12, to regulate the delivery of treatment to the patient.

More specifically, the processing and control unit uses a plurality of programmable parameters to control the delivery of electrical pulses by the pulse generator 20 to the heart 1 via lead 2.

Also shown in FIG. 1 is a remote computer 22 which can be used to store information such as the serial numbers, passwords, programming of various cardiac rhythm management devices 10. Such a remote computer 22 can be used to control the programmer 16 and reprogram cardiac rhythm management devices 10 via the programmer 16. The remote computer 22 can also receive, process and display information related to the operation of the cardiac rhythm management device 10 or the heart 1 being treated. Other specific features of the remote computer 22 are discussed herein below.

During the manufacture of a cardiac rhythm management device 10, it is desirable that various factory settings be programmed and other information be stored both within the memory of the processing and control unit 14 of the device and external thereto. Thus, the device 10 of the present invention has an initial start-up mode. The flow chart presented as FIG. 2 is intended to describe this mode of operation.

Figure 2:
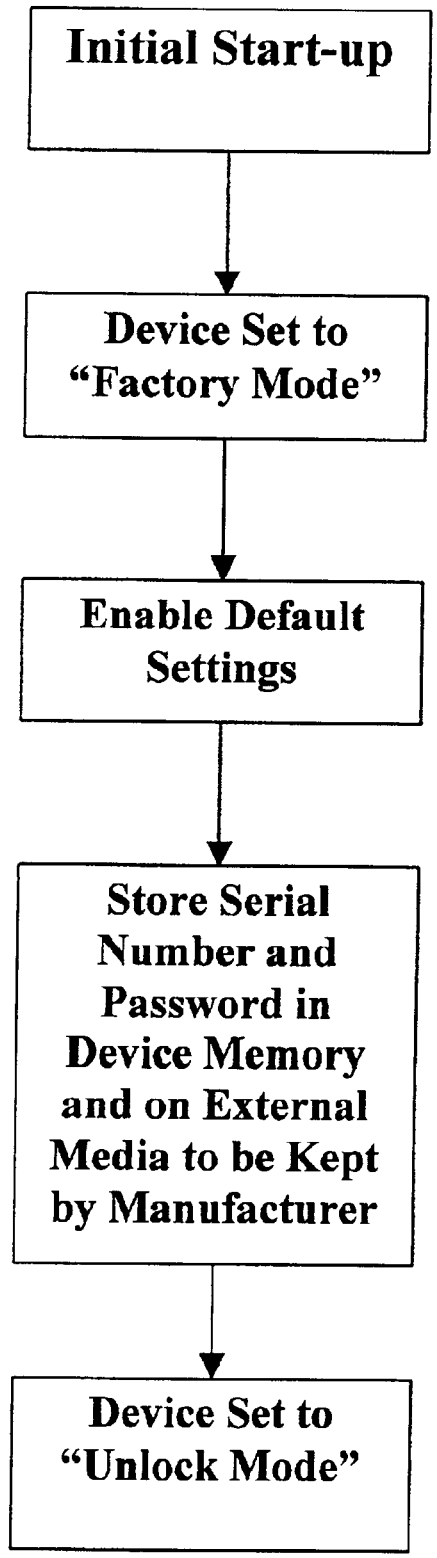
FIG. 2 is a flow chart related to factory configuration of the software of the cardiac rhythm management device.

As shown in FIG. 2, upon initial start up of the cardiac rhythm management device 10, it is set to a "factory mode". In the factory mode, the manufacturer can enable various default or initial settings for the programming of the cardiac rhythm management device 10. As these settings are entered, a serial number and password for the device 10 can also be entered. The default or initial settings, password and serial number are then stored in at least two separate places, the first being in the memory of the processing and control unit 14 of the device 10 and the second being external to the device 10 itself so that this information can be accessed by an authorized physician.

More specifically, serial numbers, passwords and other data can be stored on a disk by the external programmer 16 and/or transmitted to a remote computer 22 maintained by the manufacturer. If it is stored on a disk, the disk would typically be shipped along with the cardiac rhythm device 10 to the physician who will be surgically implanting the device 10 so that the physician has this information and can use it to program the device to meet the patient's needs. Of course, since the serial number and password remain readable from the unlocked device, it is not necessary to provide the password separately from the device because a physician using a programmer can download such data from the device's memory and store it on some suitable medium. Alternatively, the physician could use an external programmer 16 to download the information from the remote computer 22 or from the cardiac rhythm management device 10. In any event, and as shown in FIG. 2, once the serial number and password have been stored both in the device 10 and externally, the device 10 switches from the "factory mode" to the "unlock mode". The cardiac rhythm management device 10 will typically remain in the unlock mode until implantation and programming of the device by the physician is complete.

Figure 3:
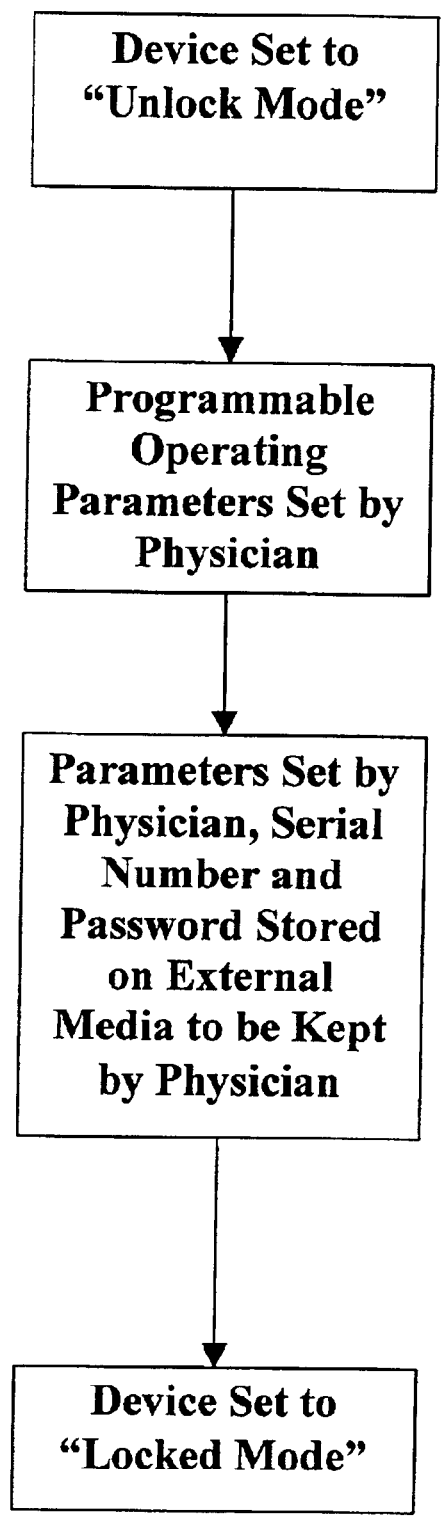
FIG. 3 is a flow chart related to programming by a physician of the cardiac rhythm management device in the "unlocked mode".

In the "unlock mode" the serial number and password cannot be changed. Some of the programming options available in the factory mode may also be disabled. Most programming features that a physician would need to access are enabled in the unlocked mode. The physician can, thus, implant the device 10 and do the normal programming and testing of the device 10 typically done at implant. With reference to FIG. 3, this process will now be explained.

With the device 10 in the "unlock mode", the physician is able to program the device 10 and set the operating parameters desired to meet the individual needs of the patient. Once testing of the device is complete and the desired parameters have been programmed, the parameters, password and serial numbers are sent by the programming and control unit 14 via the telemetry 18 to the external programmer 16. Preferably, this data will be stored on a disk by the external programmer 16. The disk can then be maintained in the patient's file. A copy of the disk could be given to the patient, preferably the patient is given an identification card that includes the serial number and password of the implanted device along with other information. Also, if additional passwords have been set, the data can be transmitted via some means, for example, the Internet or worldwide web, to the remote computer 22 maintained by the manufacturer.

At this point in the process, the physician has a choice. The physician can leave the device 10 in the unlocked mode so that the physician and others can reprogram the device without any need for the password or serial number. Alternatively, and for security reasons, the physician can switch the device 10 to its locked mode of operation. Once in the locked mode, the password is required to switch the cardiac rhythm management device back to the unlocked mode. To fully understand the benefits of the present invention, it must be understood that in the unlocked mode, a full range of features can be accessed and reprogrammed by the physician. This can be referred to as "unlock mode feature set". It also must be understood that in the locked mode a far more limited set of features can be accessed or reprogrammed. This more limited set of features is referred to as the "locked mode feature set". For example, in the locked mode one might still be able to interrogate the processing and control unit 14 of the devices 10 to determine (a) the status of the device 10; (b) a history related to the operation of the device 10; or (c) the activities of the heart 1. In the locked mode, a physician might also be able to temporarily program the device 10 to a safe state for emergency room procedures. In the locked mode, however, one cannot read the password, nor reprogram most of the features of device 10. If so desired, the ability to download history data stored in memory can also be blocked. Also, test features of the device 10 (such as features designed to induce a cardiac condition for test purposes) are not available.

Figure 4:
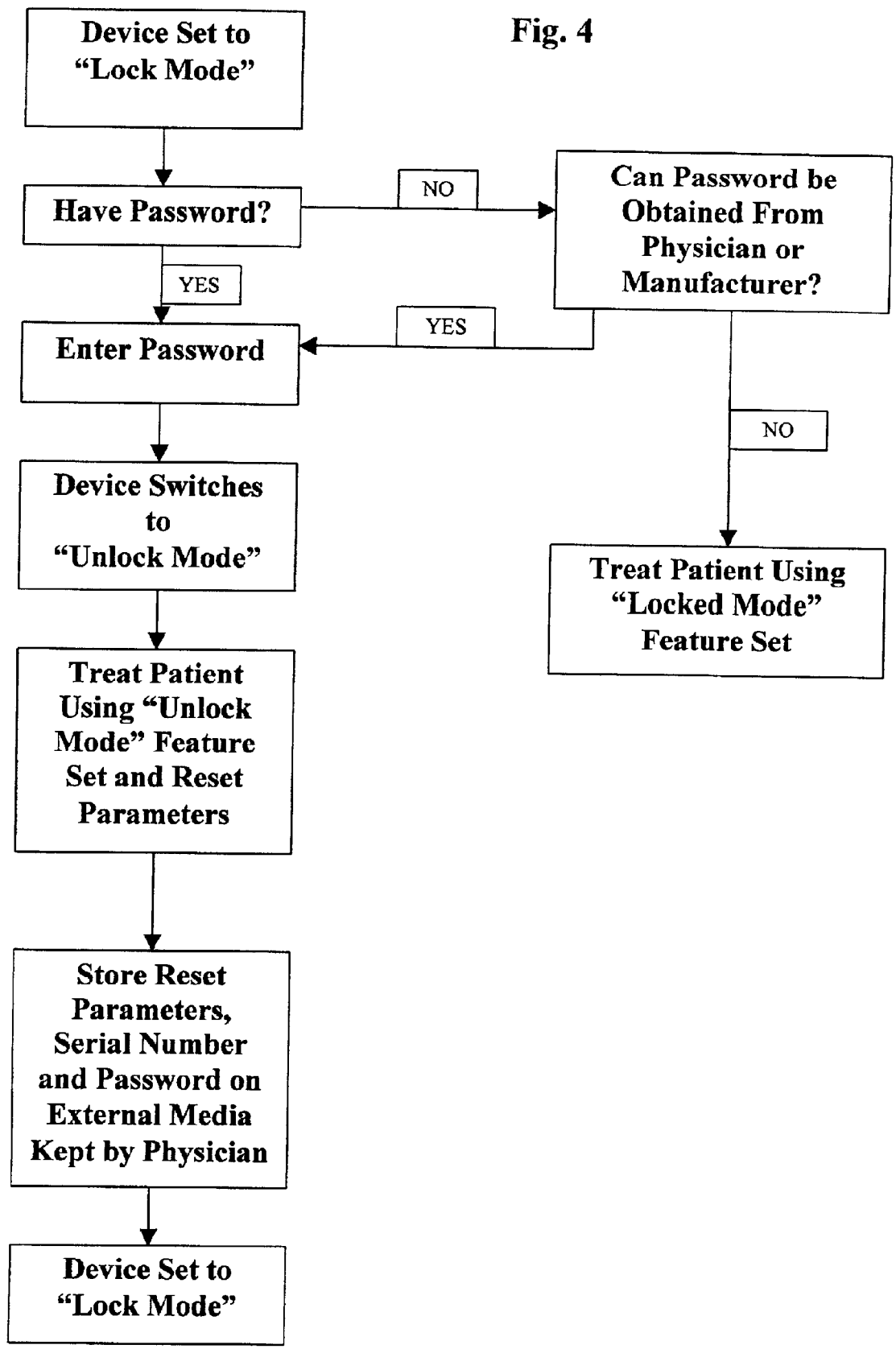
FIG. 4 is a flow chart related to programming by a physician of the cardiac rhythm management device when it is in the "locked mode".

FIG. 4 is intended to provide a brief but clear description of the operation of the cardiac rhythm management device 10 when it is in the "lock mode". If a physician has the password and wishes to place the device 10 in the unlocked mode, he uses the external programmer 16 to deliver the password to the processing and control unit 14 via telemetry 18. The processing and control unit 14 compares the password stored in its memory with the password transmitted by the programmer 16. If they match, the device 10 switches to the unlock mode and the unlock mode feature set is available to the physician for treating the patient and reprogramming the device 10. Once reprogramming has been completed, the new parameters as well as the serial number and password are stored on external media such as a diskette. These new parameters can also be transmitted by the external programmer 16 to the remote computer 22. The physician then can return the device 10 to the locked mode.

Alternatively, if the particular physician treating the patient does not know the password, that physician can contact the manufacturer or the physician who implanted the device 10 for the password. The password can be obtained via telephone voice communication. Alternatively, the password can be obtained via data communication between the treating physician's external programmer and the manufacturer's remote computer 22. The password could also be obtained from the patient if the patient has a copy of the disk or the identification card on which it was stored. In either event, various security checks are present to ensure that the password is not delivered to unauthorized personnel.

Once the treating physician has obtained the password, he or she can then enter the password into the external programmer 16 which transmits it to the processing and control unit 14 via telemetry 18. A comparison is done between the password stored in the memory of the processing and control unit 14 and the password received via telemetry. If there is a match, the device 10 switches to the unlock mode.

If for any reason the treating physician cannot obtain and enter the correct password, the device 10 will remain in the locked mode and only the locked mode feature set will be available to the physician for use in treating the patient.

As indicated above, a significant advantage of this invention is that it can allow physicians to access data stored in the cardiac rhythm management device 10 and even reprogram the device 10 from very distant locations. For example, the patient could have a programmer 16 in their home coupled in some fashion to the Internet. A physician, from a terminal also coupled to the Internet, could communicate with the device 10. The physician could be across the street, across town, across the country, or even over seas. In such a situation, security is of paramount importance to ensure the health and safety of the patient. The security system of the present invention provides the requisite security to ensure the safety of the patient.

It is also important to note that the programmer 16 can be of the sophisticated type used at hospitals and clinics. To save costs, however, it can be far more simple. All that is required is that the programmer serve as part of the communications link between the treating physician and the cardiac rhythm management device 10. The programmer 16 could be something as simple as a transceiver attached to a port of a personal computer connected to the Internet. Alternatively, the programmer 16 could have its own addressable Internet connection, other network connection, or modem so that it can communicate, via the Internet or otherwise, with equipment at the physician's location. This connection can be wired or wireless. In this context, the physician would use equipment, such as remote computer 22, at his or her end to supply the programmer 16 with the password which the programmer 16 sends to the cardiac rhythm management device 10. The remote computer 22 could also be used to (1) process and display data transmitted by the telemetry 18 of the cardiac rhythm management device 10 to the programmer 16; and (2) control the programming signals that the programmer 16 sends to the cardiac rhythm management device 10 to change the parameters used to control the device 10. The programmer 16, itself, would merely serve as a transceiver for communication with the cardiac rhythm management device 10.

The discussion set forth above describes the security system of the present invention in very basic terms. Refinements can be made to further improve security.

For example, the above description contemplates three programming modes—factory, unlocked and locked. Additional programming modes, each made having a different accessible feature set and requiring a different password can also be employed without deviating from the present invention.

The device 10 can also have an auto-lock feature. If this feature is desired, the device 10 will automatically go into the lock mode if there is no programmer activity for a predetermined period of time.

The device 10 or programmer 16 can be provided with a security alarm that sounds or is illuminated if multiple wrong passwords are entered. The alarm could also be actuated if one attempts to utilize features that are part of the unlocked mode feature set when the device 10 is in the locked mode.

Likewise, the device 10 could be provided with a lock-out feature. This feature would prevent the device 10 from switching modes for a predetermined period of time after a predetermined number of failed attempts to enter the correct password.

The memory of the device 10 could also be used to store the serial number of all programmers that were used to switch the device to the unlock mode or that were used in a failed attempt to place the device 10 in the unlocked mode.

Of course, there may be emergency situations where a physician, who does not know the password, must be able to change the operation of the device 10 to effectively and promptly treat the patient. This can be accommodated in several ways. For example, various features can be made available for a limited period of time even in the locked mode. The device 10 could permit a physician to enable a limited number of stat shocks while the device 10 is in the locked mode. The device 10 could also permit the physician to disable tachycardia therapy or bradycardia therapy while the device is locked for a predetermined period of time. Alternatively, a master password could be made available which would enable some features of the locked feature set without enabling all such features.

In the event that the correct password cannot be determined or if the data stored in the memory of the processing and control unit 14 related to the password is somehow corrupted, a long, complicated, secure and time-consuming procedure could be used to return the device 10 to the "factory mode" or some other mode in which the device can be reprogrammed and a new password assigned.

As an alternative to the security system described above or to enhance the efficacy of the security system, one could apply a similar password protection scheme to the external programmer 16. Each programmer 16 could be assigned a password that would need to be entered before the programmer would send a password or programming signals to the cardiac rhythm management device. Similar password protection could be applied to other communications and processing equipment in the chain between the doctor and patient.

In the simplest embodiment there would be a single password for the programmer. Alternatively, each user of the programmer could be assigned his or her own unique password. This would not only provide security but would also enable the programmer to identify and track who used the programmer to program which cardiac rhythm management devices. Different users could also be given rights to different feature sets depending upon their training and experience. If user tracking were not deemed to be important, the programmer could be set up to accept different shared passwords to provide access to different feature sets. This alternative would make it easier to set up the security system of the programmer as is part of the manufacturing process. However, a user-based password system would not involve a particularly difficult set-up process for the owner of the external programmer. An administrative password would be set up at the factory and the owner, knowing the administrative password, could set up different user passwords and assign various rights to each user. Whichever password protection scheme was applied to the programmer, passwords and serial numbers for the programmer could be stored on the remote computer 22 or a diskette or even on the programmer itself in a memory location only accessible to someone knowing the administrative password, if needed for future reference.

Those skilled in the art will appreciate that security would be improved if one had to know both the password for the programmer 16 and the password for the cardiac rhythm management device 10 in order to be able to reprogram the cardiac rhythm management device 10 or gain access to history data or the like stored in the memory of the cardiac rhythm management device 10.

The foregoing is intended to provide a sufficient description of the best mode of the invention to enable those skilled in the art to practice the invention. The invention is not intended to be limited to cardiac rhythm management devices. It also has application for other programmable medical devices. Various modifications can be made without departing from the scope of the invention which is defined by the following claims.

What is claimed:

1. A implantable and programmable medical device comprising:
   a. a processing and control unit for regulating the delivery of treatment to a patient in accordance with a plurality of programmable parameters, said processing and control unit having (1) memory in which a password and programmable parameters are stored, (2) a first mode of operation in which a first set of said programmable parameters stored in memory can be changed, and (3) a second mode of operation in which at least one of said first set of said programmable parameters cannot be changed; and
   b. an external programmer for transmitting passwords and programming signals to said processing and control unit such that if a password transmitted by the eternal external programmer matches the password stored in the memory of the processing and control unit, the processing and control unit will switch to said first mode of operation so that the programming signals can be used to change any of the first set of programmable parameters stored in memory.

2. The programmable medical device of claim 1 wherein said processing and control unit has a third mode of, operation in which said password and a serial number can be set and stored in said memory.

3. The programmable medical device of claim 2 wherein said external programmer can interrogate the memory of the processing and control unit to determine and record said password when the processing and control unit is in either said first or third modes of operation, but not while said processing and control unit is in said second mode of operation.

4. The programmable medical device of claim 2 further comprising a remote computer in which the password and serial number are stored for future reference.

5. The programmable medical device of claim 2 wherein said external programming means can interrogate the memory of the processing and control means to determine and record said password when the processing and control means is in either said first or third modes of operation, but not while said processing and control means is in said second mode of operation.

6. The programmable medical device of claim 2 further comprising a remote storage and computing means for storing the password and serial numbers of said processing and control means for future reference.

7. The programmable medical device of claim 1 and further comprising media on which said password is recorded, said media capable of being carried by a patient being treated with said implantable medical device.

8. The programmable medical device of claim 7 wherein said media comprises an identification card.

9. The programmable medical device of claim 1 wherein said password, once stored in memory, cannot be changed in either said first or said second modes of operation.

10. The programmable medical device of claim 9 wherein said password is set at the factory during manufacture of the device.

11. The programmable medical device of claim 1 wherein said processing and control unit will not switch to said first mode of operation for a predetermined period of time if said external programmer transmits a predetermined number of passwords that do not match the password stored in the memory of the processing and control unit.

12. The programmable medical device of claim 1 further including an alarm which will be activated if the external programmer transmits a predetermined number of passwords that do not match the password stored in the memory of the processing and control unit.

13. The programmable medical device of claim 12 when said alarm is audible.

14. The programmable medical device of claim 12 wherein said alarm is visual.

15. The programmable medical device of claim 1 wherein said processing and control means has a third mode of operation in which said password and a serial number can be set and stored in memory.

16. A programmable medical device comprising:
   a. a processing and control unit for regulating the delivery of treatment to a patient in accordance with a plurality of programmable parameters, said processing and control unit having (1) a first mode of operation in which a serial number and password can be entered and stored in its memory, (2) a second mode of operation in which a first set of operating parameters can be entered and stored in its memory, and (3) a third mode of operation in which at least one of said first set of operating parameters cannot be altered;
   b. an external programmer for transmitting passwords and programming signals to said processing control unit such that if a password transmitted by the eternal external programmer matches the password stored in the memory of the processing and control unit, the processing and control unit will switch to said second mode of operation so that the programming signals can be used to change th any of the first set of operating parameters stored in the memory of the processing and control unit, the external programmer automatically reading and storing the serial number and password of the processing and control unit if said processing and control unit is in said second mode of operation.

17. The programmable medical device of claim 16 wherein said external programmer automatically reads and stores the serial number and password of the processing and control unit if said processing and control unit is in said first mode of operation.

18. The programmable medical device of claim 16 wherein said external programmer cannot read and store the serial number and password of the processing and control unit if said processing and control unit is in said third mode of operation.

19. A programmable medical device comprising:
   a. a processing and control unit for regulating the delivery of treatment to a patient in accordance with a plurality of programmable parameters, said processing and control unit having (1) a first mode of operation in which a serial number and Password can be entered and stored in its memory, (2) a second mode of operation in which a first set of operating parameters can be entered and stored in its memory, and (3) a third mode of operation in which at least one of said first set of operating parameters cannot be altered;
   b. an external programmer for transmitting passwords and programming signals to said processing control unit such that if a password transmitted by the external programmer matches the password stored in the memory of the processing and control unit, the processing and control unit will switch to said second mode of operation so that the programming signals can be used to change any of the first set of operating parameters stored in the memory of the processing and control unit, external programmer reads the serial number of the processing and control unit, interrogates the remote storage/computer to determine the serial number of the processing and control unit and transmits the password to the processing and control unit to switch the processing and control unit from the third mode of operation to the second mode of operation for reprogramming; and
   c. a remote computer in which the password and serial number are stored for future reference.

20. The programmable medical device of claim 19 wherein said external programming means reads the serial number of the processing and control means, interrogates the remote storage and computing means to determine the serial number of the processing and control means, and transmits the password to the processing and control means to switch the processing and control means from the third mode of operation to the second mode of operation for reprogramming.

21. The programmable medical device of claim 16 wherein, when said processing and control unit is in said second mode of operation the external programmer can be used to change the parameters of said first set of operating parameters which can be altered when said processing and control unit is in said third mode of operation.

22. The programmable medical device of claim 16 wherein said processing and control unit will automatically switch from said second mode of operation to said third mode of operation after a predetermined period of time if no programming signals are received from the external programmer.

23. The programmable medical device of claim 16 wherein said external programmer can be controlled from a remote computer.

24. The programmable medical device of claim 23 wherein said external programmer is connected to said remote computer via a network.

25. The programmable medical device of claim 16 further comprising a remote storage and computing means in which the password and serial number are stored for future reference.

26. The programmable medical device of claim 16 wherein when said processing and control means is in said second mode of operation the external programming means can be used to change the parameters of said first set of operating parameters which can be altered when said processing and control means is in said third mode of operation.

27. The programmable medical device of claim 19 wherein said processing and control means will automatically switch from said second mode of operation to said third mode of operation after a predetermined period of time if no programming signals are received from the external programming means.

28. The programmable medical device of claim 19 wherein said external programmer can be controlled from a remote computer.

29. A programmable medical device comprising:
   a. processing and control means for regulating the delivery of treatment to a patient in accordance with a plurality of programmable parameters, said processing and control means having (1) memory in which a password and programmable parameters are stored, (2) a first mode of operation in which a first set of said programmable parameters stored in memory can be changed, and (3) a second mode of operation in which at least one of said first set of said programmable parameters cannot be changed; and
   b. external programming means for transmitting passwords and programming signals to said processing control unit such that if a password transmitted by the eternal programming means matches the password stored in the memory of the processing and control means, the processing and control means will switch to said first mode of operation so that the programming signals can be used to change any of the first set of programmable parameters stored in memory.

30. A programmable medical device comprising:
   a. processing and control means for regulating the delivery of treatment to a patient in accordance with a plurality of programmable parameters, said processing and control means having (1) a first mode of operation in which a serial number and password can be entered and stored in its memory, (2) a second mode of operation in which a first set of operating parameters can be entered and stored in its memory, and (3) a third mode of operation in which at least one of said first set of operating parameters cannot be altered;
   b. external programming means for transmitting passwords and programming signals to said processing and control means such that if a password transmitted by the eternal programming means matches the password stored in the memory of the processing and control means, the processing and control means will switch to said second mode of operation so that the programming signals can be used to change the any of the first set of operating parameters stored in the memory of the processing and control means.

31. A method for protecting a programmable medical device from unauthorized programming, said method comprising:
   a. providing a processing and control unit that controls the operation of the medical device, said processing and control unit having memory for storing a password and operating parameters, said processing and control unit having at least a first mode of operation in which all of a first set of operating parameters can be altered and a second mode of operation in which less than all of said first set of operation parameters can be altered, said password being used to control the entry of the processing and control unit into the first mode of operation;

b. providing an external programmer capable of transmitting passwords and programming signals to said processing and control unit;

c. using the external programmer to send a password to the processing and control unit which compares the password sent to the password stored in its memory, and enters the first mode of operation only if the password stored in memory and the password transmitted match;

d. if the processing and control unit is in the first mode of operation, using the external programmer to alter at least one of the first set of parameters.

32. The method of claim 31 further comprising the step of interrogating a remote computer to determine the password that the external programmer sends to the processing unit.

33. The method of claim 32 further comprising the step of using a remote computer to control the operation of the programmer.

34. The method of claim 32 wherein said remote computer communicates with the external programmer via a network.

35. The method of claim 34 wherein the remote computer must transmit the correct password in order to control the external programmer and use it to alter operating parameters stored in the memory of the processing and control unit.

36. A programmable medical device comprising a processing and control unit for regulating the delivery of treatment to a patient in accordance with a plurality of programmable parameters, said processing and control unit having a password assigned to it so that at least some of the programmable parameters can only be altered in response to programming signals from an external programmer if the processing and control unit first receives from the external programmer a password corresponding to the password assigned to the processing and control unit.

37. The programmable medical device of claim 36 further comprising an external programmer having means for comparing a password assigned to the external programmer with a password entered into the external programmer so that at least some programming signals will not be transmitted by the external programmer to the processing and control unit if the password assigned to the external programmer does not match the password entered into the external programmer.

38. The programmable medical device of claim 36 wherein said programmable medical device is implantable.

39. The programmable medical device of claim 36 wherein said password assigned to the processing and control unit, once stored in memory, cannot be changed.

40. The programmable medical device of claim 39 wherein said password is set at the factory during manufacture of the device.

41. The programmable medical device of claim 36 further comprising media on which said password assigned to the processing and control unit is recorded, said media capable of being carried by a patient being treated with said implantable medical device.

42. The programmable medical device of claim 41 wherein said media is an identification card.

43. The programmable medical device of claim 36 wherein said processing and control unit will not permit programmable parameters to be altered for a predetermined period of time if the processing and control unit receives from an external programmer a predetermined number of passwords that do not match the password assigned to the processing and control unit.

44. The programmable medical device of claim 36 further including an alarm which will be activated if the processing and control unit receives a predetermined number of passwords that do not match the password assigned to the processing and control unit.

45. The programmable medical device of claim 44 wherein said alarm is audible.

46. The programmable medical device of claim 44 wherein said alarm is visual.

* * * * *

UNITED STATES PATENT AND TRADEMARK OFFICE
CERTIFICATE OF CORRECTION

PATENT NO. : 6,880,085 B1
DATED : April 12, 2005
INVENTOR(S) : Ronald A. Balczewski et al.

It is certified that error appears in the above-identified patent and that said Letters Patent is hereby corrected as shown below:

Column 7,
Line 44, the word "eternal" should be deleted.

Column 8,
Line 57, the letters "th" should be deleted.

Column 9,
Line 11, the word "Password" should read -- password --.

Signed and Sealed this

Twelfth Day of July, 2005

JON W. DUDAS
*Director of the United States Patent and Trademark Office*